(12) United States Patent
Jones (10) Patent No.: US 8,764,756 B2
(45) Date of Patent: Jul. 1, 2014

(54) SINGLE ACTION ANTI-TORQUE ROD REDUCER

(75) Inventor: Scott Jones, McMurray, PA (US)

(73) Assignee: K2M, Inc., Leesburg, VA (US)

( * ) Notice: Subject to any disclaimer, the term of this patent is extended or adjusted under 35 U.S.C. 154(b) by 184 days.

(21) Appl. No.: 13/402,557

(22) Filed: Feb. 22, 2012

(65) Prior Publication Data

US 2012/0215266 A1 Aug. 23, 2012

Related U.S. Application Data

(60) Provisional application No. 61/445,288, filed on Feb. 22, 2011.

(51) Int. Cl.
*A61B 17/70* (2006.01)

(52) U.S. Cl.
USPC ..................................... 606/86 A

(58) Field of Classification Search
USPC ............... 606/86 A, 279, 99, 104, 205–208; 81/443–446, 452–455
See application file for complete search history.

(56) References Cited

U.S. PATENT DOCUMENTS

| | | | |
|---|---|---|---|
| 2,248,054 A | 7/1941 | Becker | |
| 3,604,487 A | 9/1971 | Gilbert | |
| 5,020,519 A | 6/1991 | Hayes et al. | |
| 5,466,243 A | 11/1995 | Schmieding et al. | |
| 5,910,141 A | 6/1999 | Morrison et al. | |
| 6,416,521 B1 | 7/2002 | Waldner et al. | |
| 6,440,133 B1 | 8/2002 | Beale et al. | |
| 6,648,888 B1 | 11/2003 | Shluzas | |
| 6,660,006 B2 | 12/2003 | Markworth et al. | |
| 6,790,209 B2 | 9/2004 | Beale et al. | |
| 2003/0225408 A1 | 12/2003 | Nichols et al. | |
| 2004/0215190 A1 | 10/2004 | Nguyen et al. | |
| 2005/0143749 A1 | 6/2005 | Zalenski et al. | |
| 2005/0149053 A1 | 7/2005 | Varieur et al. | |
| 2005/0192587 A1 | 9/2005 | Lim | |
| 2005/0192589 A1 | 9/2005 | Raymond et al. | |
| 2005/0261702 A1 | 11/2005 | Oribe et al. | |
| 2006/0036260 A1 | 2/2006 | Runco et al. | |
| 2006/0074418 A1 | 4/2006 | Jackson | |
| 2006/0089651 A1 | 4/2006 | Trudeau et al. | |
| 2006/0200132 A1 | 9/2006 | Chao et al. | |
| 2007/0213722 A1 | 9/2007 | Jones et al. | |
| 2008/0172062 A1 | 7/2008 | Donahue et al. | |

*Primary Examiner* — Mary Hoffman
(74) *Attorney, Agent, or Firm* — Carter, DeLuca, Farrell & Schmidt, LLP (57) ABSTRACT

A rod reducing device includes an elongate member, a pair of jaw members, a sleeve having a cam pin, and an actuation lever. Translation of the cam pin along the inner surfaces of the jaw members pivotally moves the jaw members between a receiving position in which distal end portions of the respective jaw members are widened and an engaging position in which the distal end portions of the respective jaw members are move toward each other to engage the head of the bone screw. The actuation lever is movable between an open in which a distal end portion of the sleeve is disposed proximal of the distal end portions of the jaw members and a closed position in which the distal end portion of the sleeve is disposed distal of the distal end portions of the jaw members for reducing the connecting rod.

32 Claims, 6 Drawing Sheets

SINGLE ACTION ANTI-TORQUE ROD REDUCER

CROSS-REFERENCE TO RELATED APPLICATION

This application claims priority to, and the benefit of, U.S. Provisional Patent Application Ser. No. 61/445,288, filed Feb. 22, 2011, the entire contents of which are incorporated by reference herein.

BACKGROUND

1. Technical Field

The present disclosure relates to an orthopedic surgical device, and more particularly, to a rod reducing device.

2. Background of Related Art

Spinal implant systems have been developed to achieve immobilization of vertebral bodies of the spine in a particular spatial relationship to correct spinal irregularities and to restore stability to traumatized areas of the spine. In one such system, one or more rods are disposed longitudinally along a length of the spine spanning two or more vertebral bodies. The rod is engaged to a number of fixation elements fixed to or engaged with the vertebrae along the spinal column. Typically, immobilization of the spinal column involves a series of bone screws and connecting rods.

The process of properly inserting a connecting rod into a receiving slot of a bone screw and then securing that connecting rod in place is both time consuming and burdensome. When bone screws in several adjacent vertebrae are to be securely connected by a connecting rod, the repeated process of inserting the connecting rod into the head of the one screw and then securing the connecting rod in place for each respective bone screw can be even more difficult.

Accordingly, there is a need for a device that facilitates the process of putting in place the connecting rod into each bone screw, while the bone screw is held in a stable configuration to avoid the application of additional torque to the bone screw and the bone into which the screw is inserted when the locking cap is secured into position.

SUMMARY

In accordance with the present disclosure, there is provided a rod reducing device for reducing or urging a connecting rod into position with a head of a bone screw. The rod reducing device includes an elongate member defining a lumen therethrough, a pair of opposing jaw members pivotally associated with the elongate member, a sleeve slidably surrounding at least partially the elongate member and the pair of opposing jaw members, and an actuation lever pivotably mounted on the elongate member. The sleeve also defines a longitudinal passage therethrough. The sleeve further includes a cam pin configured to engage inner surfaces of the pair of opposing jaw members. In particular, translation of the cam pin along the inner surfaces of the pair of opposing jaw members pivotally moves the pair of opposing jaw members between a receiving position in which distal end portions of the respective pair of opposing jaw members are widened to receive the head of the bone screw therebetween and an engaging position in which the distal end portions of the respective pair of opposing jaw members are move toward each other to engage the head of the bone screw therebetween. The actuation lever is operatively coupled to the sleeve. In particular, the actuation lever is movable between open and closed positions. In the open position, a distal end portion of the sleeve is disposed proximal of the distal end portions of the pair of opposing jaw members in the receiving position. In the closed position, the distal end portion of the sleeve is disposed distal of the distal end portions of the pair of opposing jaw members in the engaging position.

In another embodiment, the actuation lever may be offset with respect to the longitudinal axis defined by the elongate member when in the open position and may be aligned with the longitudinal axis when in the closed position.

In still another embodiment, the rod reducing device may further include a knob rotatable about the sleeve, wherein rotation of the knob axially adjusts a distance of travel of the sleeve by the actuation lever. The knob may be rotatable between a first position adapted to reduce a first rod connector having a first diameter and a second position adapted to reduce a second rod connector having a second diameter.

In yet another embodiment, the lumen of the elongate member may be configured and dimensioned for passage of a bone screw locking cap and an instrument for tightening the locking cap into place with the bone screw.

In yet another embodiment, the rod reducing device may further include a linkage member interconnecting the actuation lever with the sleeve.

In still yet another embodiment, the pair of opposing jaw members may be configured to securely grasp a head of the bone screw when the actuation lever is in the closed position. In particular, each of the pair of opposing jaw members may include a protrusion, and the elongate member may define a pair of sockets configured and dimensioned for pivotal engagement of the respective protrusions of the pair of opposing jaw members therein.

In still yet another embodiment, the sleeve may define a pair of opposing slots dimensioned to receive the pair of opposing jaw members therethrough, respectively.

In yet another embodiment, the inner surfaces of the pair of opposing jaw members may each include an inner camming surface extending radially inward from the inner surface. The cam pin may engage the respective inner camming surfaces when the actuation lever is in the open position, thereby urging the pair of opposing jaw members toward the receiving position. In particular, the inner camming surface may be disposed at a proximal portion of the respective pair of opposing jaw members. Each of the pair of opposing jaw members may further include an outer surface having an outer camming surface extending radially outward from the outer surface. The sleeve may engage the outer camming surfaces when the actuation lever is in the closed position, thereby urging the pair of opposing jaw members toward the engaging position.

In still yet another embodiment, the cam pin may be fixed securely with the sleeve for a single body movement with the sleeve.

In yet another embodiment, the rod reducing device may further include a biasing member to urge the sleeve to move proximally when the actuation lever is in the closed position.

In yet another embodiment, the cam pin may conform to the contour of the lumen of the elongate member to facilitate passage of a screw cap therethrough.

In yet another embodiment, the distal end portion of the sleeve may include a connecting rod drive member configured and adapted to at least partially receive the connecting rod therein.

BRIEF DESCRIPTION OF THE DRAWINGS

Various embodiments of the present disclosure are described hereinbelow with reference to the drawings, wherein.

DETAILED DESCRIPTION OF EMBODIMENTS

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

Figure 1:
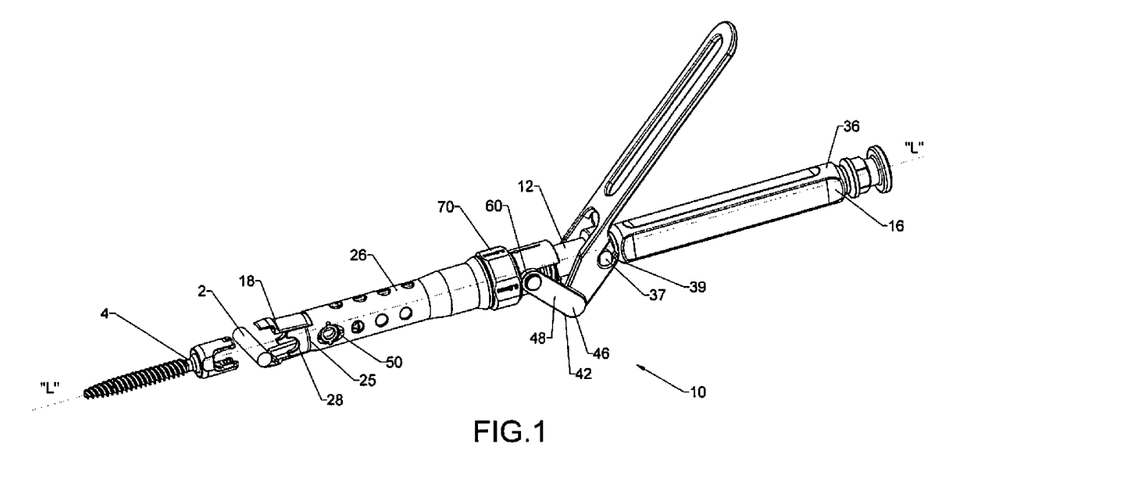
FIG. 1 is a perspective view of a rod reducing device in accordance with an embodiment of the present disclosure illustrating an open configuration.
Figure 2:
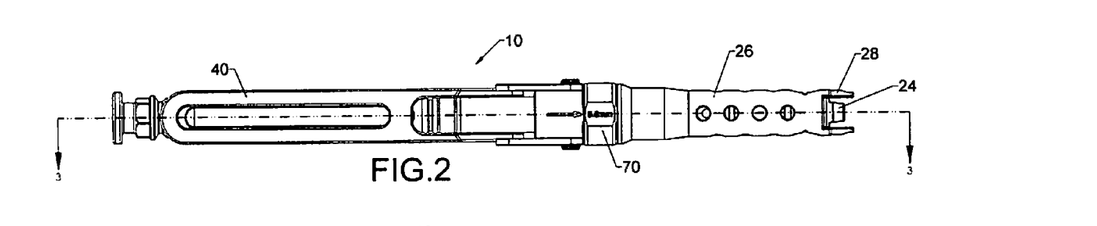
FIG. 2 is a top view of the rod reducing device of FIG. 1 in a closed configuration.

With reference to FIG. 1, an embodiment of the present disclosure is shown generally as a rod reducing device 10 including a housing 12 defining a lumen 14 therethrough (FIG. 3), a sleeve 26, and an actuation lever 40. Lumen 14 is configured and dimensioned for passage of a bone screw locking cap (not shown) and an instrument (not shown) for positioning and securely tightening the locking cap into place in the locking cap receptacle of a bone screw 4. Sleeve 26 is circumferentially and slidably disposed around at least a distal portion of housing 12. Actuation lever 40 is pivotably mounted to housing 12, whereby actuation lever 40 is movable between an open configuration (FIG. 1) in which actuation lever 40 is offset with respect to a longitudinal axis "L-L" defined by rod reducing device 10 and a closed configuration (FIG. 9) in which actuation lever 40 is aligned (i.e., parallel) with longitudinal axis "L-L."

With continued reference to FIG. 1, a force transfer arm 48 operatively interconnects actuation lever 40 with sleeve 26, such that the pivotal movement of actuation lever 40 from the open configuration to the closed configuration slidably moves sleeve 26 along an outer surface of housing 12 to a position where a distal end portion 25 of sleeve 26 can contact and reduce a connecting rod 2 into a rod receiving notch in the head of bone screw 4, as will be described in detail below. In addition, grasping elements 24 of jaw members 80 (FIG. 3) grip bone screw 4, and facilitate alignment of rod reducing device 10 with bone screw 4, as will be described in detail below.

A screw head having a rod receiving notch is disclosed in commonly assigned U.S. patent application Ser. Nos. 11/493,624 and 11/493,625, the complete disclosures of which are fully incorporated herein by reference. An example of a rod reducer is disclosed in commonly assigned U.S. Pat. No. 7,771,430, the entire contents of which are fully incorporated herein by reference.

Figure 7:
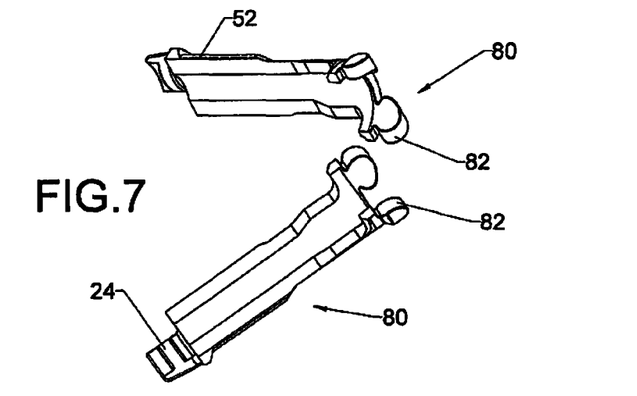
FIG. 7 is a perspective view of a pair of jaw members for use with the rod reducing device of FIG. 1.

With reference now to FIGS. 1-4, housing 12 includes a handle portion 36 and body portion 17 (FIG. 3) extending distally from handle portion 36. Distal end portion 18 of housing 12 securely engages bone screw 4 and facilitates alignment of rod reducing device 10 with bone screw 4. Specifically, body portion 17 includes at a distal portion thereof a pair of jaw members 80 (FIG. 7) each having a grasping element 24 for securely holding bone screw 4 in place relative to rod reducing device 10. Jaw members 80 diametrically oppose each other and each jaw member 80 conforms to the contour of lumen 14. Moreover, each jaw member 80 includes protrusions 82 (FIGS. 10 and 11) that correspond to sockets 90 (FIGS. 10 and 11) defined in a distal end portion of body portion 17 of housing 12 for secure attachment to body portion 17. In particular, each socket 90 is configured and dimensioned for pivotal engagement of the respective protrusion of the pair of opposing jaw members therein such that each jaw is pivotable about a separate pivot axis and the pivot axis is substantially transverse to a longitudinal axis of the rod reducing device 10. In this manner, grasping elements 24 of respective jaw members 80 may move toward and away from each other to facilitate engagement and disengagement with bone screw 4. In addition, body portion 17 may define a plurality of bores 88 to reduce the overall weight of device 10, while maintaining sufficient compressive strength to withstand transferring force applied to the outer surface of body portion 17, as well as to grasping elements 24 of jaw member 80.

Figure 10:
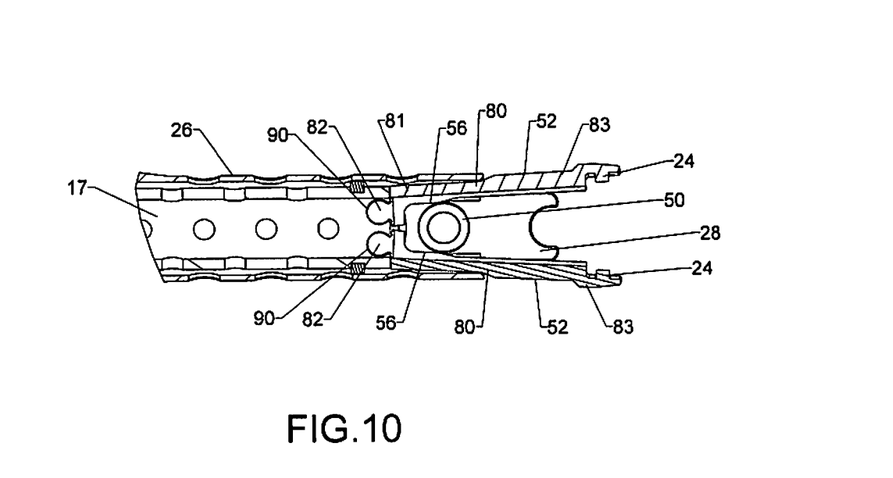
FIG. 10 is an enlarged partial longitudinal cross-sectional view of a distal end portion of the rod reducing device of FIG. 1 in the open configuration.
Figure 11:
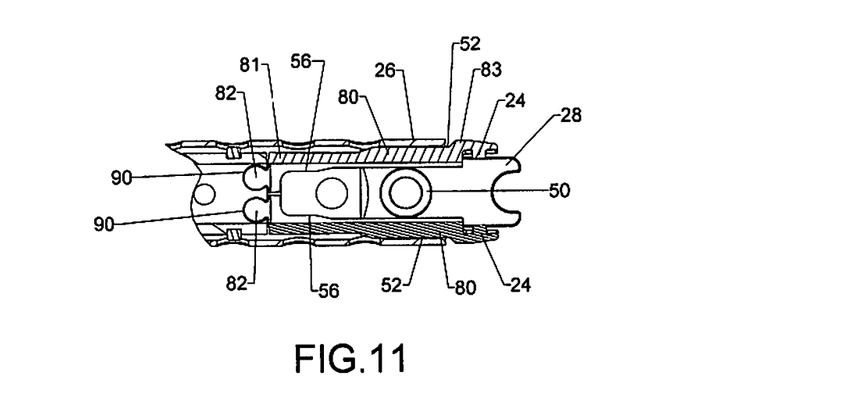
FIG. 11 is an enlarged partial longitudinal cross-sectional view of a distal end portion of the rod reducing device of FIG. 1 in the closed configuration.

With brief reference to FIGS. 10 and 11, a distal end portion 83 of jaw member 80 defines an outer cam surface 52, and a proximal end portion 81 of jaw member 80 defines an inner cam surface 56. In particular, outer cam surface 52 protrudes radially outward such that outer cam surface 52 has a greater thickness than that of a proximal end portion 81 of jaw member 80, while defining a larger diametered lumen 14 than that of proximal end portion 81 defining inner cam surface 56. On the other hand, inner cam surface 56 protrudes radially inward defining lumen 14 having a smaller diameter than that of distal end portion 83 of jaw member 80. In this manner, as sleeve 26 is translated distally over outer cam surface 52, grasping elements 24 are urged inward so as to securely engage the head of bone screw 4, as will be discussed in detail below.

Figure 3:
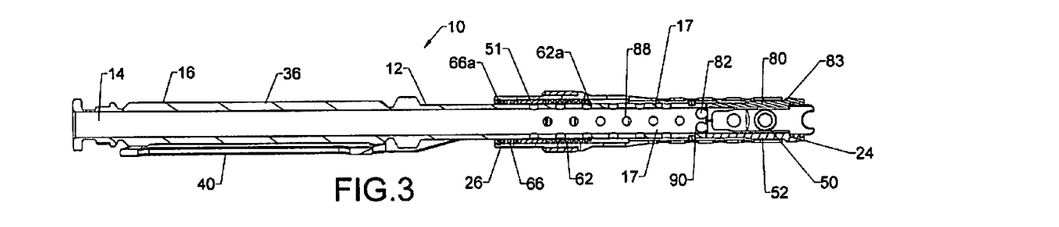
FIG. 3 is a cross-sectional view taken along section line 3-3 of FIG. 2.
Figure 4:
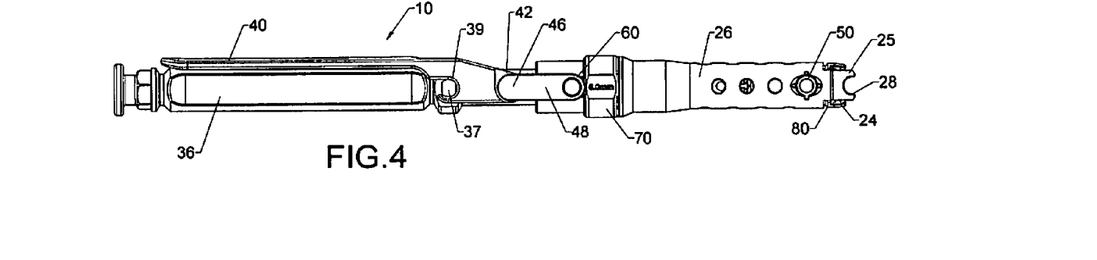
FIG. 4 is a side view of the rod reducing device of FIG. 2.

With particular reference back to FIGS. 3 and 4, when actuation lever 40 is in the closed configuration, actuation lever 40 aligns with handle portion 36 in a superposed manner. It is envisioned that handle portion 36 may define transversely recessed portions (not shown) for gripping comfort and placement of the fingers. Housing 12 further includes a lateral pin 37 (FIG. 4) on each lateral side of housing 12 adjacent a distal end of handle portion 36 and proximal of sleeve 26. Lateral pin 37 is configured and dimensioned to be received in a pivot socket or hook portion 39 defined in actuation lever 40 to enable pivotal movement of actuation lever 40 about lateral pin 37.

With particular reference to FIGS. 1 and 4, a distal end portion 42 of actuation lever 40 is further pivotably associated with a proximal end 46 of force transfer arm 48, and a distal end 60 of force transfer arm 48 is pivotally coupled to sleeve 26. In this manner, when the surgeon activates actuation lever 40 in the open configuration (FIG. 1) by squeezing it against handle portion 36 of housing 12, actuation lever 40 pivots about lateral pin 37, whereby distal end portion 42 of actuation lever 40 aligns with housing 12. Such movement causes further alignment of force transfer arm 48 with actuation lever 40, which in turn moves sleeve 26 distally. As sleeve 26 is moved distally, distal end portion 25 of sleeve 26 makes contact with a properly positioned connecting rod 2. In this manner, connecting rod 2 is urged distally into position with the rod receiving notch of the screw head, while the screw head is held stationary.

Figures 5, 6:
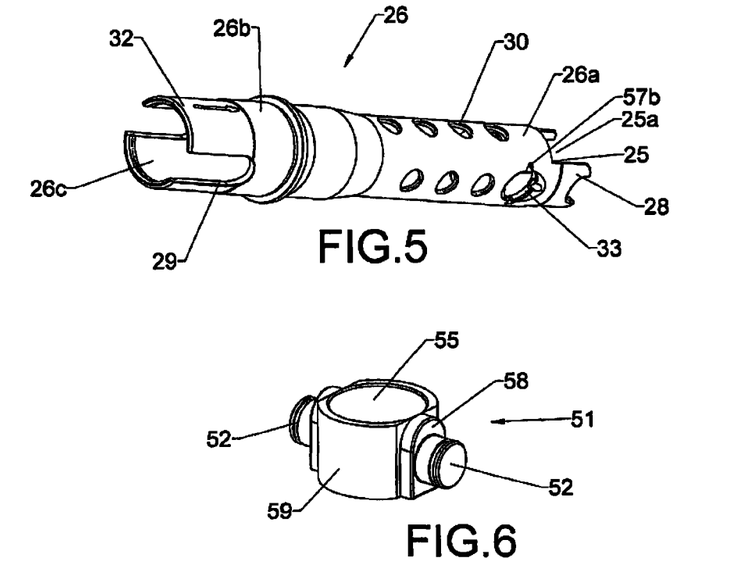
FIG. 5 is perspective view of a sleeve of the rod reducing device of FIG. 1.
FIG. 6 is a perspective view of a trunnion for use with the sleeve of FIG. 5.

With reference now to FIGS. 5 and 6, sleeve 26 includes a body portion 26a, a neck portion 26b extending proximally from body portion 26a and connecting rod drive members 28 protruding distally from body portion 26a. In particular, distal end portion 25 of sleeve 26 defines a pair of opposing recesses 25a interposed between connecting rod drive members 28. Recesses 25a are configured and dimensioned to receive at least partially jaw members 80, as will be discussed in detail below. Moreover, sleeve 26 defines a lumen 26c therethrough for passage of the bone screw locking cap and the instrument for positioning and securely tightening the locking cap into place in the locking cap receptacle of bone screw 4.

Sleeve 26 is circumferentially and slidably disposed around at least a lower portion of housing 12. In particular, neck portion 26b of sleeve 26 defines a pair of diametrically opposed slits 29. Lumen 26c defined in neck portion 26b of sleeve 26 is adapted and dimensioned to receive therein a trunnion 51 (FIG. 6). Trunnion 51 includes diametrically opposing guides 58 on an outer wall 59 thereof and a pair of pins 52 that extend radially outward from a respective guide 58. In addition, trunnion 51 defines a central bore 55. Each guide 58 is configured and dimensioned to engage slit 29 of neck portion 26b. In this manner, trunnion 51 is securely disposed within lumen 26c of neck portion 26b, such that central bore 55 of trunnion 51 is concentrically aligned with lumen 26c. In this manner, central bore 55 is able to receive therethrough body portion 17 of housing 12. Moreover, each pin 52 protrudes from the respective slit 29. Each pin 52 of trunnion 51 is pivotally connected to a respective distal end 60 of force transfer arm 48 (FIG. 4).

With brief reference back to FIG. 3, sleeve 26 may be further provided with a pair of biasing members 62, 66 positioned distal and proximal of trunnion 51, respectively. In addition, a retaining member 66a is positioned proximal of first biasing member 66 and a second retaining member 62a is positioned distal of second biasing member 62. In this manner, trunnion 51 and biasing members 66, 62 are limited to a proximal position by retaining member 66a and limited to a distal position by retaining member 62a. When actuation lever 40 is moved toward housing 12, the pivotal action of actuation lever 40 and force transfer arm 48 serves to slidably move sleeve 26 distally along the outer surface of housing 12. As sleeve 26 moves distally, biasing member 62 in contact with retaining member 62a is compressed against retaining member 62a. Compression of biasing member 62 urges sleeve 26 to slide proximally along housing 12. Similarly, as sleeve 26 moves proximally, a relatively smaller biasing member 66 is compressed against retaining member 66a which slightly urges sleeve 26 to slide distally along housing 12.

With reference to FIG. 5, connecting rod drive members 28 protrude distally from body portion 26a. In order to facilitate contact with connecting rod 2, driving member 28 may have concave geometry complementary to the arching shape of a connecting rod cross-section. In addition, each connecting rod drive members 28 of sleeve 26 is offset about 90 degrees with respect to jaw member 80 about longitudinal axis "L-L." In this manner, grasping elements 24 of jaw members 80 do not substantially overlap and interfere with connecting rod drive members 28. In this manner, when the surgeon actuates actuation lever 40, sleeve 26 travels distally and driving member 28 makes contact with connecting rod 2 such that as the screw head is held stationary by grasping elements 24 of jaw members 80 connecting rod 2 is moved distally into position with the rod receiving notch of the screw head.

Figure 8:
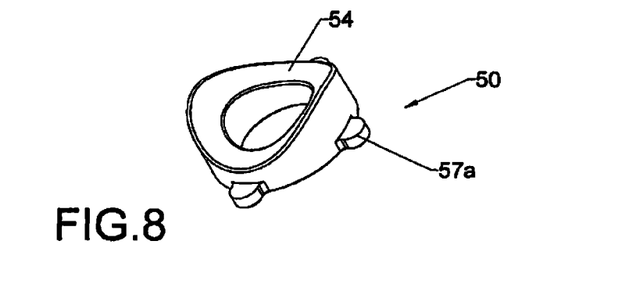
FIG. 8 is perspective view of a cam pin for use with the sleeve of the rod reducing device of FIG. 1.

With continued reference to FIG. 5, body portion 26a of sleeve 26 may define a plurality of bores 30 to reduce the overall weight of device 10 while maintaining sufficient compressive strength to withstand transferring force applied at proximal end portion 32 of sleeve 26. Sleeve 26 further defines a pair of opposing bores 33 on the lateral side of body portion 26a. In particular, the pair of opposing bores 33 are proximal of connecting rod drive members 28 and are configured and dimensioned to securely hold respective cam pin 50 (FIG. 8) therein. Each cam pin 50 is securely disposed in the respective bore 33. In particular, each cam pin 50 may include a plurality of pegs 57a extending radially outward from a periphery of cam pin 50, as shown in FIG. 8. Each bore 33 may define a plurality of recesses 57b configured and dimensioned to securely hold the plurality of pegs 57a, as shown in FIG. 5.

With particular reference back to FIGS. 10 and 11, cam pins 50 are interposed between the pair of opposing jaw members 80. Each cam pin 50 may include a concaved inner surface 54, as shown in FIG. 8. Concaved inner surface 54 of cam pin 50 may conform to the contour of lumen 14 to facilitate insertion and passage of the screw cap and/or instrument to tighten screw cap onto bone screw 4.

With particular reference to FIG. 10, when actuation lever 40 is in the open configuration, sleeve 26 is slidably moved proximally along the outer surface of housing 12 to a position where rod driving members 28 are proximal of grasping elements 24 of jaw members 80. In particular, cam pin 50 engages inner cam surface 56 and moves distal end portions 83 of jaw members 80 apart in an outward direction. In this manner, the opening defined between distal end portions 83, for example, grasping elements 24, is larger than the inner diameter of lumen 14 or an outer diameter of the head of bone screw 4. In addition, outer cam surfaces 52 of jaw members 80 extend through the respective recesses 25a defined between connecting rod drive members 28, which further aids widening of the opening created between distal end portions 83. In this manner, the surgeon need not force grasping elements 24 over the screw head, i.e., forcing the screw head between grasping elements 24, prior to actuation of actuation lever 40.

Figure 9:
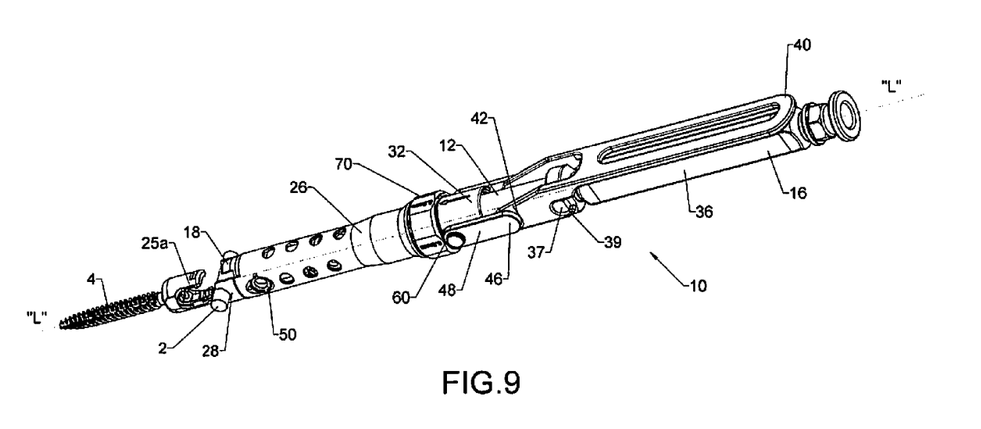
FIG. 9 is a perspective view of the rod reducing device of FIG. 1 in a closed configuration with a bone screw.

With reference now to FIGS. 9 and 11, when actuation lever 40 is actuated, sleeve 26 slidably moves distally along the outer surface of housing 12 to a position where rod driving member 28 can contact and reduce connecting rod 2 into the head of bone screw 4. In particular, the distal movement of sleeve 26 urges distal end portions 83 of jaw members 80 inward to securely engage the head of bone screw 4, as outer cam surfaces 52 of jaw members 80 are now enclosed by sleeve 26 and grasping elements 24 are disposed within respective recesses 25a defined between connecting rod drive members 28. At this time, cam pin 50 is interposed between outer cam surfaces 52, but does not engage any portion of an inner surface of jaw members 80. In this manner, reduction of connecting rod 2 into the head of bone screw 4 is facilitated by grasping elements 24 of jaw members 80, which securely grips bone screw 4 in place relative to device 10.

Figure 12:
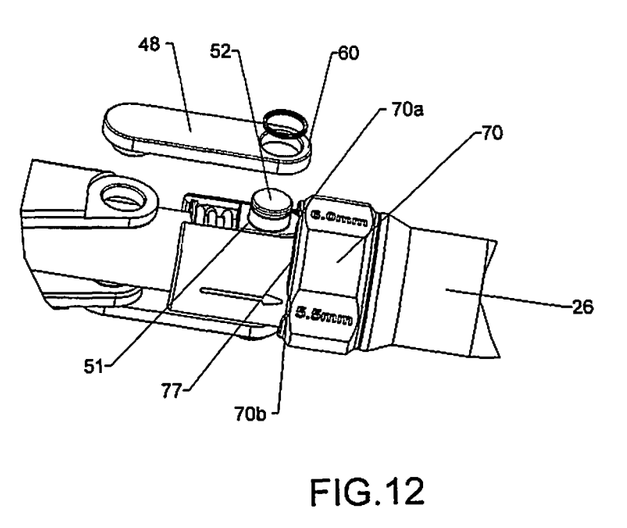
FIG. 12 is a partial perspective view of the rod reducing device of FIG. 1 with a force transfer arm separated.

With reference now to FIGS. 5 and 12, sleeve 26 further includes a knurled knob 70 rotatably mounted on neck portion 26b of sleeve 26. Knurled knob 70 is disposed distal of pin 52 of trunnion 51. Knurled knob 70 defines at least a pair of circumferentially arranged cutout portions or notches 70a, 70b adjacent a proximal end portion 77 of knurled knob 70. Cutout portions or notches 70a, 70b are configured and dimensioned to receive at least a portion of distal end 60 of force transfer arm 48 therein. In particular, each notch 70a, 70b is dimensioned for a predetermined travel distance of sleeve 26. Specifically, distal end 60 of force transfer arm 48 is adapted to be partially received in each notch 70a, 70b by a predetermined amount corresponding to the dimensions of notch 70a, 70b. In this manner, by providing a pair of notches 70a, 70b having different dimensions, the user may select a desired travel distance of sleeve 26 through a selection of a desired notch 70a, 70b by rotation of knurled knob 70. For example, knurled knob 70 as shown in FIG. 12 illustrates two settings including one for reduction of 5.5 mm diameter connection rod and another for reduction of 6 mm diameter connection rod. A selection of a smaller notch 70a enables a greater travel distance of sleeve 26 to reduce a smaller diameter connection rod. A selection of a larger notch 70b enables reduction of a larger diameter connection rod.

While the configuration as shown in FIG. 12 illustrates a setting which enables a selection between two diameters of connection rods, the knurled knob and the notch used therein may be tailored to a particular application being performed, for example, to enable compatibility with different size connection rods.

In use, a surgeon accesses the patient's spine and prepares bones to receive bone screws 4. Multiple bone screws 4 may be inserted into the bones. Thereafter, connecting rod 2 is placed adjacent to the rod receiving recess of each respective bone screw 4. Then actuation lever 40 of rod reducing device 10 is actuated to position connecting rod 2 in the receiving portion of the head of a first screw 4, while grasping elements 24 of jaw members 80 securely engage the head of the first screw 4. Thereafter, a bone screw locking cap is placed in the head of bone screw 4 through lumen 14 of rod reducing device 10 using an appropriate instrument. At this time, bone screw 4 is securely held in place by device 10 as torque is applied to the locking cap by a tightening instrument inserted through lumen 14. Rod reducing device 10 is then released from screw 4 by a reversal of the movement of actuation lever 40. In the case of revision surgery, rod reducing device 10 can be used to securely hold bone screw 4 in place while the locking cap is removed through lumen 14 of the device.

Although the illustrative embodiments of the present disclosure have been described herein with reference to the accompanying drawings, the above description, disclosure, and figures should not be construed as limiting, but merely as exemplifications of particular embodiments. For example, the pivot points such as, lateral peg 37 was positioned near the center of rod reducing device 10. However, all the pivot points shown hereinabove, may be positioned anywhere along the length of housing 12, as long as effective leverage for the actuation lever 40 may be achieved. It is to be understood, therefore, that the disclosure is not limited to those precise embodiments, and that various other changes and modifications may be effected therein by one skilled in the art without departing from the scope or spirit of the disclosure.

What is claimed is:

1. A rod reducing device for reducing a connecting rod into position with a head of a bone screw, the rod reducing device comprising:
an elongate member defining a lumen therethrough;
a pair of opposing jaw members pivotally associated with the elongate member;
a sleeve having a longitudinal passage therethrough, the sleeve slidably surrounding, at least partially, the elongate member and the pair of opposing jaw members, the sleeve including a cam pin configured to engage inner surfaces of the pair of opposing jaw members, translation of the cam pin along the inner surfaces of the pair of opposing jaw members pivotally moves the pair of opposing jaw members between a receiving position in which distal end portions of the respective pair of opposing jaw members are widened to receive the head of the bone screw therebetween and an engaging position in which the distal end portions of the respective pair of opposing jaw members are moved toward each other to engage the head of the bone screw therebetween; and
an actuation lever pivotably mounted on the elongate member, the actuation lever operatively coupled to the sleeve, the actuation lever movable between an open position in which a distal end portion of the sleeve is disposed proximal of the distal end portions of the pair of opposing jaw members in the receiving position, and a closed position in which the distal end portion of the sleeve is disposed distal of the distal end portions of the pair of opposing jaw members in the engaging position for reducing the connecting rod into position in the head of the bone screw, wherein in the open position, the actuation lever is offset with respect to a longitudinal axis defined by the elongate member and in the closed position, the actuation lever is aligned with the longitudinal axis.

2. The rod reducing device according to claim 1, further comprising a knob rotatable about the sleeve, wherein rotation of the knob axially adjusts a distance of travel of the sleeve by the actuation lever.

3. The rod reducing device according to claim 2, wherein the knob is rotatable between a first position adapted to reduce a first rod connector having a first diameter and a second position adapted to reduce a second rod connector having a second diameter.

4. The rod reducing device according to claim 1, further comprising a linkage member interconnecting the actuation lever with the sleeve.

5. The rod reducing device according to claim 1, wherein the pair of opposing jaw members is configured to securely grasp the head of the bone screw when the actuation lever is in the closed position.

6. The rod reducing device according to claim 5, wherein each of the pair of opposing jaw members includes a protrusion, and the elongate member defines a pair of sockets configured and dimensioned for pivotal engagement of the respective protrusions of the pair of opposing jaw members therein.

7. The rod reducing device according to claim 1, wherein the sleeve defines a pair of opposing slots dimensioned to receive the pair of opposing jaw members therethrough, respectively.

8. The rod reducing device according to claim 1, wherein the inner surfaces of the pair of opposing jaw members each include an inner camming surface extending radially inward from the inner surface, the cam pin engaging the respective inner camming surfaces when the actuation lever is in the open position, thereby urging the pair of opposing jaw members toward the receiving position.

9. The rod reducing device according to claim 8, wherein the inner camming surface is disposed at a proximal portion of the respective pair of opposing jaw members.

10. The rod reducing device according to claim 1, wherein each of the pair of opposing jaw members further includes an outer surface having an outer camming surface extending radially outward from the outer surface, the sleeve engaging the outer camming surfaces when the actuation lever is in the closed position, thereby urging the pair of opposing jaw members toward the engaging position.

11. The rod reducing device according to claim 10, wherein the outer camming surfaces are disposed at the respective distal end portions of the pair of opposing jaw members.

12. The rod reducing device according to claim 1, wherein the cam pin is fixed securely with the sleeve for a single body movement with the sleeve.

13. The rod reducing device according to claim 1, further comprising a biasing member to urge the sleeve to move proximally when the actuation lever is in the closed position.

14. The rod reducing device according to claim 1, wherein the cam pin conforms to the contour of the lumen of the elongate member to facilitate passage of a screw cap therethrough.

15. The rod reducing device according to claim 1, wherein the lumen of the elongate member is configured and dimensioned for passage of a bone screw locking cap and an instrument for tightening the bone screw locking cap into place with the bone screw.

16. The rod reducing device according to claim 1, wherein the distal end portion of the sleeve includes a connecting rod drive member configured and adapted to at least partially receive the connecting rod therein.

17. A rod reducing device for reducing a connecting rod into position with a head of a bone screw, the rod reducing device comprising:
   an elongate member defining a lumen therethrough;
   a pair of opposing jaw members pivotally associated with the elongate member;
   a sleeve having a longitudinal passage therethrough, the sleeve slidably surrounding, at least partially, the elongate member and the pair of opposing jaw members, the sleeve including a cam pin configured to engage inner surfaces of the pair of opposing jaw members, translation of the cam pin along the inner surfaces of the pair of opposing jaw members pivotally moves the pair of opposing jaw members between a receiving position in which distal end portions of the respective pair of opposing jaw members are widened to receive the head of the bone screw therebetween and an engaging position in which the distal end portions of the respective pair of opposing jaw members are moved toward each other to engage the head of the bone screw therebetween;
   an actuation lever pivotably mounted on the elongate member, the actuation lever operatively coupled to the sleeve, the actuation lever movable between an open position in which a distal end portion of the sleeve is disposed proximal of the distal end portions of the pair of opposing jaw members in the receiving position, and a closed position in which the distal end portion of the sleeve is disposed distal of the distal end portions of the pair of opposing jaw members in the engaging position for reducing the connecting rod into position in the head of the bone screw; and
   a knob rotatable about the sleeve, wherein rotation of the knob axially adjusts a distance of travel of the sleeve by the actuation lever.

18. The rod reducing device according to claim 17, wherein in the open position, the actuation lever is offset with respect to a longitudinal axis defined by the elongate member and in the closed position, the actuation lever is aligned with the longitudinal axis.

19. The rod reducing device according to claim 17, wherein the knob is rotatable between a first position adapted to reduce a first rod connector having a first diameter and a second position adapted to reduce a second rod connector having a second diameter.

20. The rod reducing device according to claim 17, further comprising a linkage member interconnecting the actuation lever with the sleeve.

21. The rod reducing device according to claim 17, wherein the pair of opposing jaw members is configured to securely grasp the head of the bone screw when the actuation lever is in the closed position.

22. The rod reducing device according to claim 21, wherein each of the pair of opposing jaw members includes a protrusion, and the elongate member defines a pair of sockets configured and dimensioned for pivotal engagement of the respective protrusions of the pair of opposing jaw members therein.

23. The rod reducing device according to claim 17, wherein the sleeve defines a pair of opposing slots dimensioned to receive the pair of opposing jaw members therethrough, respectively.

24. The rod reducing device according to claim 17, wherein the inner surfaces of the pair of opposing jaw members each include an inner camming surface extending radially inward from the inner surface, the cam pin engaging the respective inner camming surfaces when the actuation lever is in the open position, thereby urging the pair of opposing jaw members toward the receiving position.

25. The rod reducing device according to claim 24, wherein the inner camming surface is disposed at a proximal portion of the respective pair of opposing jaw members.

26. The rod reducing device according to claim 17, wherein each of the pair of opposing jaw members further includes an outer surface having an outer camming surface extending radially outward from the outer surface, the sleeve engaging the outer camming surfaces when the actuation lever is in the closed position, thereby urging the pair of opposing jaw members toward the engaging position.

27. The rod reducing device according to claim 26, wherein the outer camming surfaces are disposed at the respective distal end portions of the pair of opposing jaw members.

28. The rod reducing device according to claim 17, wherein the cam pin is fixed securely with the sleeve for a single body movement with the sleeve.

29. The rod reducing device according to claim 17, further comprising a biasing member to urge the sleeve to move proximally when the actuation lever is in the closed position.

30. The rod reducing device according to claim 17, wherein the cam pin conforms to the contour of the lumen of the elongate member to facilitate passage of a screw cap therethrough.

31. The rod reducing device according to claim 17, wherein the lumen of the elongate member is configured and dimensioned for passage of a bone screw locking cap and an instrument for tightening the bone screw locking cap into place with the bone screw.

32. The rod reducing device according to claim 17, wherein the distal end portion of the sleeve includes a connecting rod drive member configured to at least partially receive the connecting rod therein.

* * * * *